United States Patent
Miller et al.

(10) Patent No.: US 6,690,466 B2
(45) Date of Patent: *Feb. 10, 2004

(54) SPECTRAL IMAGING SYSTEM

(75) Inventors: Peter J. Miller, Newburyport, MA (US); Clifford C. Hoyt, Needham, MA (US)

(73) Assignee: Cambridge Research & Instrumentation, Inc., Woburn, MA (US)

(*) Notice: Subject to any disclaimer, the term of this patent is extended or adjusted under 35 U.S.C. 154(b) by 173 days.

This patent is subject to a terminal disclaimer.

(21) Appl. No.: 09/921,040

(22) Filed: Aug. 2, 2001

(65) Prior Publication Data

US 2002/0001080 A1  Jan. 3, 2002

Related U.S. Application Data

(63) Continuation of application No. 09/633,417, filed on Aug. 7, 2000.
(60) Provisional application No. 60/147,636, filed on Aug. 6, 1999.

(51) Int. Cl.$^7$ .................................................. G01J 3/36
(52) U.S. Cl. ....................................... 356/326; 356/328
(58) Field of Search ................................. 356/326, 328

(56) References Cited

U.S. PATENT DOCUMENTS

| | | | |
|---|---|---|---|
| 4,379,233 A | | 4/1983 | Rosenthal |
| 4,669,878 A | * | 6/1987 | Meier ........................... 356/319 |
| 4,800,279 A | | 1/1989 | Hieftji et al. |
| 5,029,245 A | | 7/1991 | Keranen et al. |

(List continued on next page.)

OTHER PUBLICATIONS

W.C. Sweatt et al., "ISIS; An Information–Efficient Spectral Imaging System," Imaging Spectrometry IV, Proc. SPIE, vol. 3438, pp. 98–106, San Diego, 1998.

B.R. Stallard, Contstruction of Filter Vectors for the Information–Efficient Spectral Imaging Sensor, Imaging Spectroscopy IV, Proc. SPIE, Vol 3438, pp. 172–182, San Diego, 1998.

(List continued on next page.)

Primary Examiner—Zandra V. Smith
(74) Attorney, Agent, or Firm—Fish & Richardson P.C.

(57) ABSTRACT

An imaging system is disclosed comprising an illuminator which produces illumination of any desired pure wavelength or of any selected mixture of pure wavelengths simultaneously, which illuminates a sample without spatio-spectral artifacts using illumination optics designed for that purpose; imaging optics, which form an image of the sample at a detector or viewing port; and a detector. This enables imaging the complete spectral image cube for a sample by taking sequential images while illuminating with a series of pure wavelengths, with greater ease and economy than by means of tunable filters, interferometers and the like. It further enables imaging while the sample is illuminated with a precisely controlled mixture of illuminant wavelengths, so that the image presented to the detector is a linear superposition of the sample properties at many wavelengths. This enables taking images of a sample' that directly measure the weighted spectral properties such as projection pursuit vectors, principal components, and the like. Data acquisition is enormously simplified, and speed is increased by one to two orders of magnitude over existing techniques. This is of great benefit in pathology, immunohistochemistry, Pap smear analysis, endoscopy, counterfeit detection, quality control, and other areas where one wishes to measure a spectral index of a living or inert sample.

41 Claims, 5 Drawing Sheets

U.S. PATENT DOCUMENTS

Figure 1:
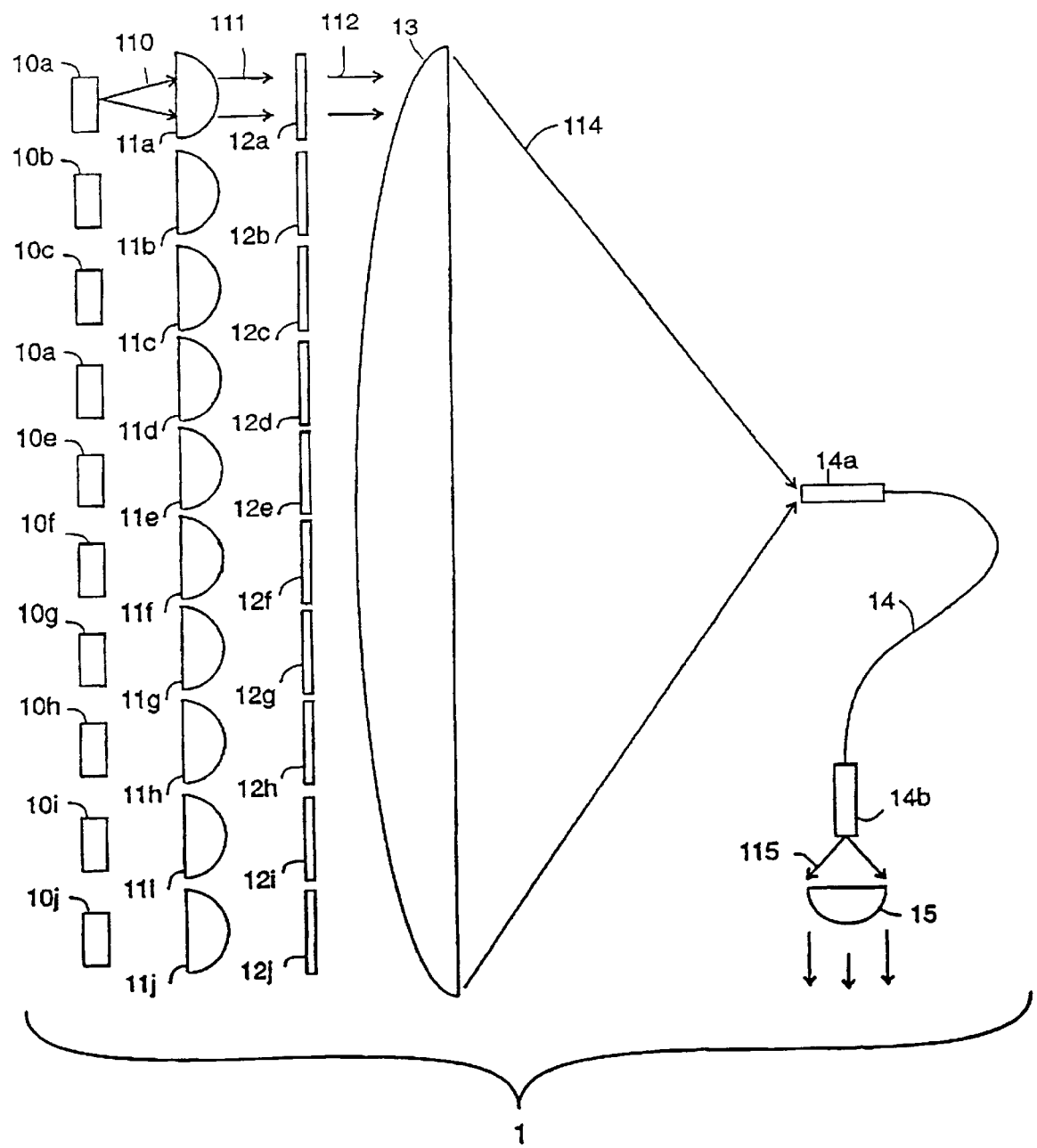

| | | | |
|---|---|---|---|
| 5,042,893 | A | 8/1991 | Ong |
| 5,137,364 | A | 8/1992 | McCarthy |
| 5,424,545 | A | 6/1995 | Block et al. |
| 5,433,197 | A | 7/1995 | Stark |
| 5,539,517 | A | 7/1996 | Cabib et al. |
| 5,567,937 | A | 10/1996 | Pinkus |
| 5,608,213 | A | 3/1997 | Pinkus et al. |
| 5,719,024 | A | 2/1998 | Cabib et al. |
| 5,760,407 | A | 6/1998 | Margosiak et al. |
| 5,838,451 | A | 11/1998 | McCarthy |
| 6,075,595 | A | 6/2000 | Malinen |
| 6,142,629 | A | 11/2000 | Adel et al. |
| 6,373,568 | B1 * | 4/2002 | Miller et al. ................ 356/326 |

OTHER PUBLICATIONS

L.O. Jimenez et al., "High Dimensional Feature Reduction via Projection Pursuit," TR–ECE 96–5, School of Electrical Engineering, Purdue University, West Lafayette, IN 47907–1285, Apr., 1995.

Hyvarien et al., "Novel Spectroscopic Techniques for Biomedical Applications," Optoelectronics Laboratory, Finland, SPIE vol. 2084, pp. 224–230.

Keraanen et al., "Thirty–two Channel LED Array Spectrometer Module with Compact Optomechanical Construction," Technical Research Centre of Finland, Electronics Laboratory, Finland, SPIE vol. 1533 Optomechanics and Dimensional Stability (1991), pp. 122–128.

Gentry et al., Biomedical Applications of the Information–Efficient Spectral Imaging Sensor (ISIS), Gentry, SPIE vol. 3603, pp. 129–142.

Shnitser et al., "Spectrally Adaptive Light Filtering," Physical Optics Corporation, Torrance, CA, SPIE vol. 3140, pp. 117–127.

Stallard et al., "Construction of Filter Vectors for the Information–Efficient Spectral Imaging Sensor," Sandia National Laboratories, Albuquerque, NM, SPIE vol. 3438, pp. 172–182.

Sweatt et al., "ISIS: An Information–Efficient Spectral Imaging System," Sandia National Laboratories, Albuquerque, NM, SPIE Vo. 3438, pp. 98–106.

Jimenez et al., "Supervised Classification in High Dimensional Space: Geometrical, Statistical and Asymptotical Properties of Multivariate Data," IEEE Transactions on Geoscience and Remote Sensing, vol. 37, No. 6, Nov. 1999; Project in Pursuit in Hyperspectral Data Anlysis, Jimenez & Landgrebe, Nov. 23, 1999, pp. 1–32.

* cited by examiner

SPECTRAL IMAGING SYSTEM

RELATED APPLICATIONS

This application is a continuation application of U.S. application Ser. No. 09/633,417 filed Aug. 7, 2000, which claims priority from U.S. Provisional Application No. 60/147,636 filed Aug. 6, 1999. Both applications being incorporated herein by reference.

BACKGROUND OF THE INVENTION

In this application, a spectral weighting function that indicates the presence or amount of a certain trait in a sample is termed a spectral index, spectral weighted index or spectral measure for that trait. The term spectral measure is also sometimes used to denote the measurement value obtained at a given point or region according to a given spectral weighting function.

Various spectral imaging systems are used to derive spectral information about samples, including imaging spectrometers, imaging interferometers, band-sequential cameras using e.g. filter wheels, and linear-variable filter imagers. Those systems which are based on linear-variable filters or on spectrometers generally acquire data about a single point or line at a time, and optical or mechanical means are used to develop a two-dimensional image of the sample. In many cases, a fully-populated image cube is obtained, consisting of an image of the sample at each adjacent spectral band in the spectral region of interest. With interferomieters, linear-variable filters and most spectrometers, there is no way to avoid acquiring the full image cube, even if only a portion of the cube is desired. Data requirements are enormous: for high-resolution images (2048×3072 pixels, 12 bits/pixel) with 32 spectral bands, nearly 400 megabytes of data must be acquired and processed. Filter wheels enable selective acquisition of the wavelengths of interest, so a sparsely populated cube may be obtained. However, if there are N bands of interest, a minimum of N exposures is still required. This is quite time-consuming and inefficient.

Spectral measures have been developed that utilize many spectral bands to describe a sample attribute, or to classify regions within a sample. An example is described in "Biomedical Applications Of The Information-Efficient Spectral Imaging Sensor (ISIS)", Gentry, Steven M.; Levenson, Richard M. Proc. SPIE Vol. 3603, p. 129–142 (1999), which describes a technique called projection pursuit that relies on a specific weighting of various spectral bands to derive an enhanced detection of sample properties. Other well-known methods such as principal component analysis involve generating spectrally-weighted sums with precise control over the weighting function.

Gentry also describes an imaging system which he terms an information-efficient spectral imaging system (ISIS). ISIS provides means for imaging a line of the sample at a time through a dispersive element, followed by an element that selectively transmits light in each spectral band according to a desired transmission amount, then a detector which determines the spectrally-weighted signal content at each pixel along the line. This produces an optically-weighted signal at the detector, rather than requiring digitization of each spectral component followed by numerical integration. While efficient in that sense, which is a great advance over the prior art of interferometry or band-sequential filters, it only images a line at a time and so requires several thousand exposures to produce a two-dimensional image. Stepping or scanning means must be provided as well, to sweep across the sample.

Use of lamps and mechanically-tuned gratings to produce monochromatic light, and thus to obtain spectral images, is well-known in the art.

The use of red, green and blue LEDs for illumination is known in the art, both in time-sequential fashion or simultaneously. The colors produced by such systems are broad, illdefined, and would not be suitable for applications that involve precise quantitative spectral measures or indicia.

For example, in U.S. Pat. No. 5,838,451, McCarthy teaches the use of a handful of LEDs with broad spectral outputs (40 nm or more) to illuminate a sample, either singly or in combination to approximate standard functions such as the tristimulus curves. These are used to construct a colorimeter. To ensure stability in time, the temperature of the LEDS is precisely regulated. Such a system is unsuitable for spectroscopic measurements, nor can it obtain accurate images of spatial distributions within objects because the illumination patterns of the various LEDs are not spatially alike.

McCarthy teaches in U.S. Pat. No. 5,137,364 a system wherein two or more LEDs with different broad emission spectra are used to illuminate a sample and the resultant light is imaged by two or more photosensors, each of which has a different spectral responsivity. The source LEDs are turned on one at a time in sequence, and the photosensor readings are noted in each case. From the table containing readings from each photosensor under each of the illumination conditions, and a calibration, various spectral and/or colorimetric estimates of the sample are obtained.

U.S. Pat. Nos. 5,608,213 and 5,567,937 describe the use of infrared LEDs as scene simulators to test night-vision goggles with a mixture of wavelengths that approximate terrestrial scenes.

The use of an array of LEDs with a current switch, along with optics including a dispersive element such as a prism or grating, to produce light of time-sequential wavelength which illuminates samples for subsequent spectral analysis is described in U.S. Pat. No. 5,029,245 issued to Keranen.

A subsequent patent, U.S. Pat. No. 6,075,595, uses the same apparatus as Keranen and further incorporates a substrate with embossed dimple-shaped light concentrators in which the LEDs are mounted, to restrict the angles at which light emerges from the LEDs and passes into the collection optics. This is said to enhance brightness and reduce scatter.

Further discussion of LED array illuminators are contained in "Novel Spectroscopic Techniques For Biomedical Applications", Hyvarinen, T.; Aikio, M.; Esko, H.; Malinen, J.; Proc. SPIE Vol. 2084, p. 224–230 (1994); and "Thirty-Two Channel Led Array Spectrometer Module With Compact Optomechanical Construction", Malinen, J.; Keranen, H.; Hannula, T.; Hyvarinen, T., in "Optomechanics And Dimensional Stability; Proceedings Of The Meeting", San Diego, Calif., Jul. 25, 26, 1991, pp. 122–128 (1991).

Ken Spring of the N.I.H. has demonstrated a system that uses three or four LEDs for time-sequential excitation of fluorescent samples at distinct excitation wavelengths. The optical arrangement collimates the emission from each LED and then passes it through a bandpass filter to define a spectral band. The collimated light from the several LEDs is introduced into the pupil plane of a telescope, which accepts light from whichever LED is lit, and feeds it into a multi-mode fiber. The fiber spatially scrambles the light and removes any inhomogeneities, after which the light emerges from the fiber and is re-imaged to illuminate the fluorescent sample. This system creates light that is essentially monochromatic at any point in time.

There is nowhere disclosed in the prior art a means for imaging a two-dimensional sample so as to directly obtain an image of some spectral index at every point in the sample. Nor does the prior art teach means for interactively determining such a spectral index from a first sample or region of a sample, then imaging other two-dimensional regions or samples according to that spectral index, except through the use of interferometers or band-sequential filters to obtain image cubes or the equivalent, each time an image is desired.

It is an object of the present invention to provide a system and method for obtaining images that reveal the precise value of potentially complicated spectral indices at every point in a two-dimensional image, without need for acquiring a complete image cube. It is another object to provide means for determining these spectral indices in situ, along with means for calibrating or compensating for the spectral response of the optics and detector used in the measurement. It is yet a further object to take advantage of spectral indices derived using techniques such as projection pursuit, principal component analysis, and the like, to distinguish between species or quantify amounts of species within a sample. A further aim is to achieve these ends in an instrument of low cost and low complexity, with no moving parts. Yet another goal is that the invention can obtain RGB color images to provide reference images of a sample, using the same apparatus as is employed for imaging spectral indicia.

Overall, it is the goal of this invention to provide an integrated system which can provide RGB imagery; which can provide precise band-by-band measurement of standard spectral indices such as photometric and calorimetric indices; which can take full spectral image cubes of a sample; which can determine quantitative, potentially complicated spectral indices from image cubes; which can perform precise calibration; and which can then rapidly image a sample using the spectral indices of interest.

SUMMARY OF THE INVENTION

The invention comprises using the light from a spectral illuminator to illuminate a sample whose detailed spectral properties are sought. The spectral illuminator can provide light having any desired distribution of wavelengths across a broad range. It provides for independently and electronically selecting the amount of light in each of many independent wavelength bands. All bands may be on, with precisely chosen amounts of light in each band. Or, only a few bands may on at a given time, or only a single band. Near-IR versions are possible as well.

By taking a sequence of images as the illuminator is controlled to provide monochromatic light in one wavelength band after another, a spectral image cube may be obtained. Optimum signal to noise may be obtained, since the amount of light used in 'each exposure can be tailored via the illuminator to make use of the full dynamic range of the detector, despite spectrally varying response in the detector and other optical elements.

The invention further has as its aim to provide for directly taking images of a spectral weighted index in a sample, without need for taking an image in each individual band then numerically weighting and summing. The spectral illuminator can be used to provide an illuminant that has precisely the spectral index as its illumination spectrum, at which point a picture may be taken that immediately records the weighted index of interest.

Since the illuminator can provide pure spectral bands as well as complex weighted spectral distributions, it provides the means for optimizing and calibrating the measurements and systems described above. It is known that detectors have a spectral response which must be accomodated in order to acquire a spectral index from a sample; the detector response can be measured by a series of monochromatic measurements using the spectral illuminator. So the illuminator may be used to correct for spectral artifacts in the rest of the optical system where its use is envisioned. In addition, the detector may be used to correct for nonlinearities, if any, in the illuminator. The photodiode sensors used in modern CMOS, CCD, and CID detectors are linear over a flux range spanning 5 orders of magnitude. To the extent that the illuminator's intensity response in a given band is nonlinear, it may be measured and corrected via the detector. When all bands are linear, and the spectral response of the system (detector plus optics) is known, then it is possible to produce precisely calibrated illumination spectra at will.

Finally, in many cases one does not know the desired spectral weighting function a priori and it must be determined. The illuminator can be used to collect an image cube of a reference or test sample, from which all spectral bands are collected. The data from this image cube is analyzed to determine the spectral weighting function, by means of principal component analysis, projection pursuit, matched filtration, or any chosen method. This weighting function is then programmed into the spectral illuminator, so images using this weighting function may then be directly collected from subsequent samples. The same illuminator may be used for determining the weighting function, and for obtaining the images of the samples using this spectral weighting index.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE DRAWINGS

Figure 2:
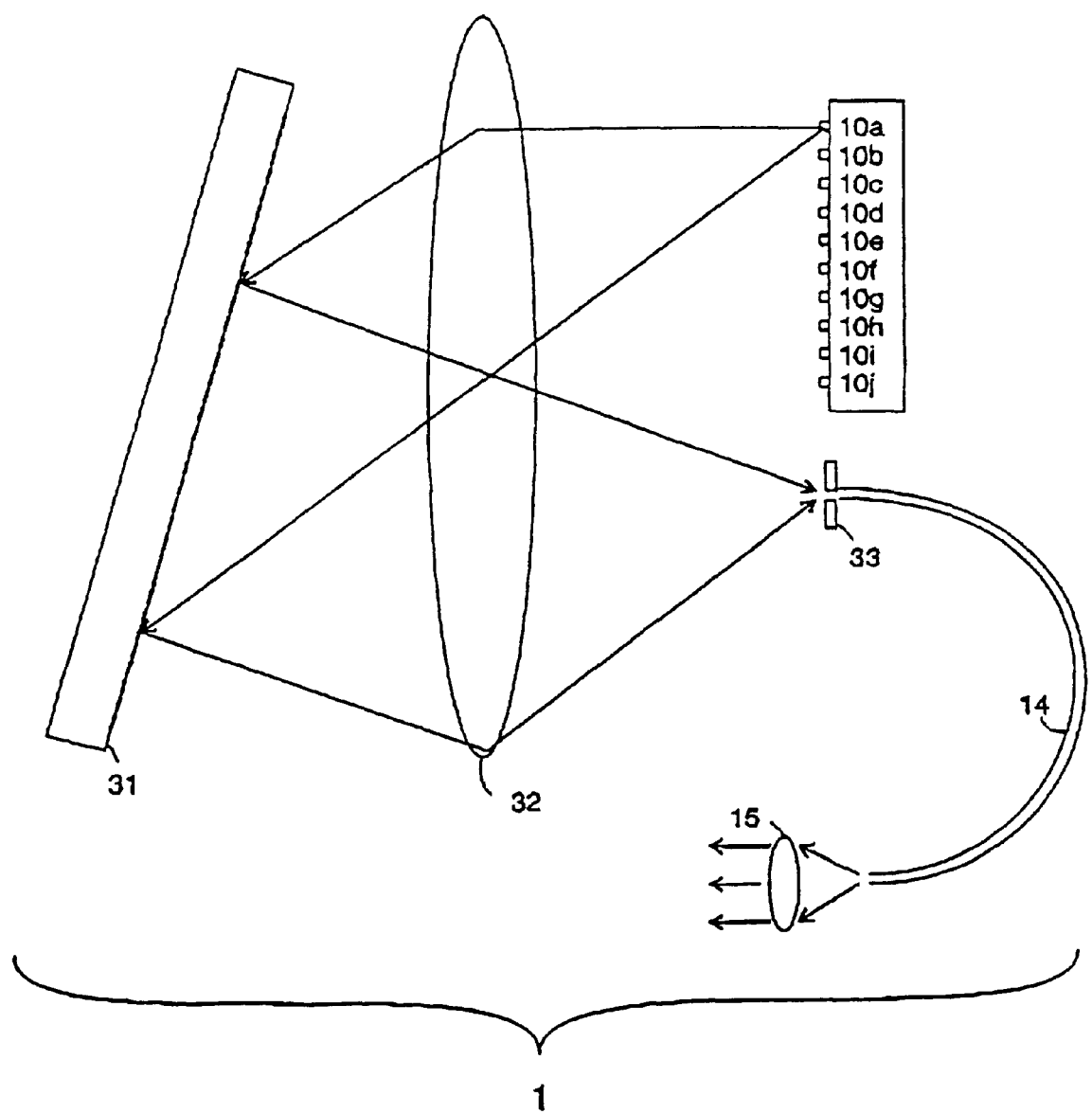
Figure 3:
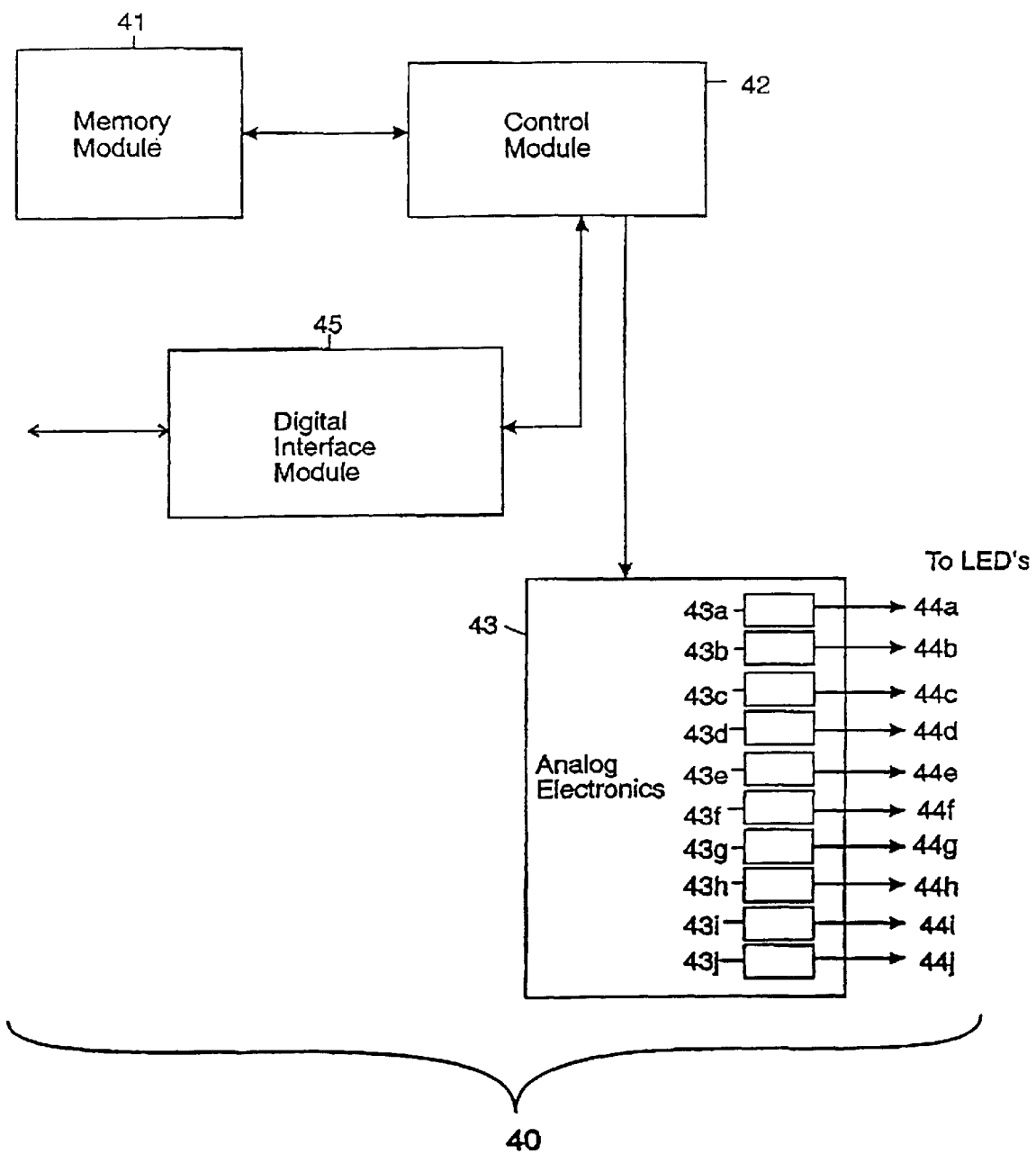
Figure 4A:
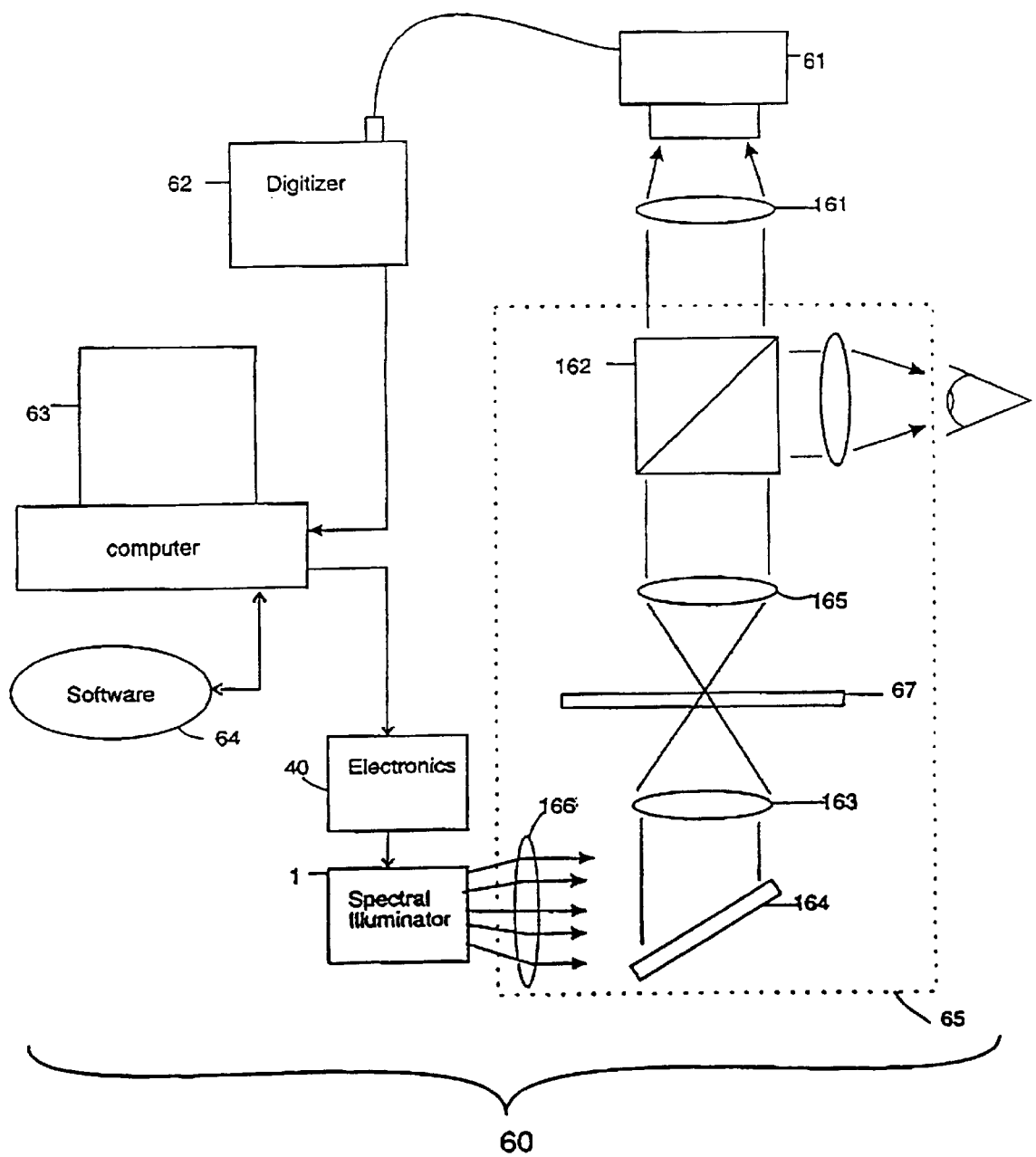
Figure 4B:
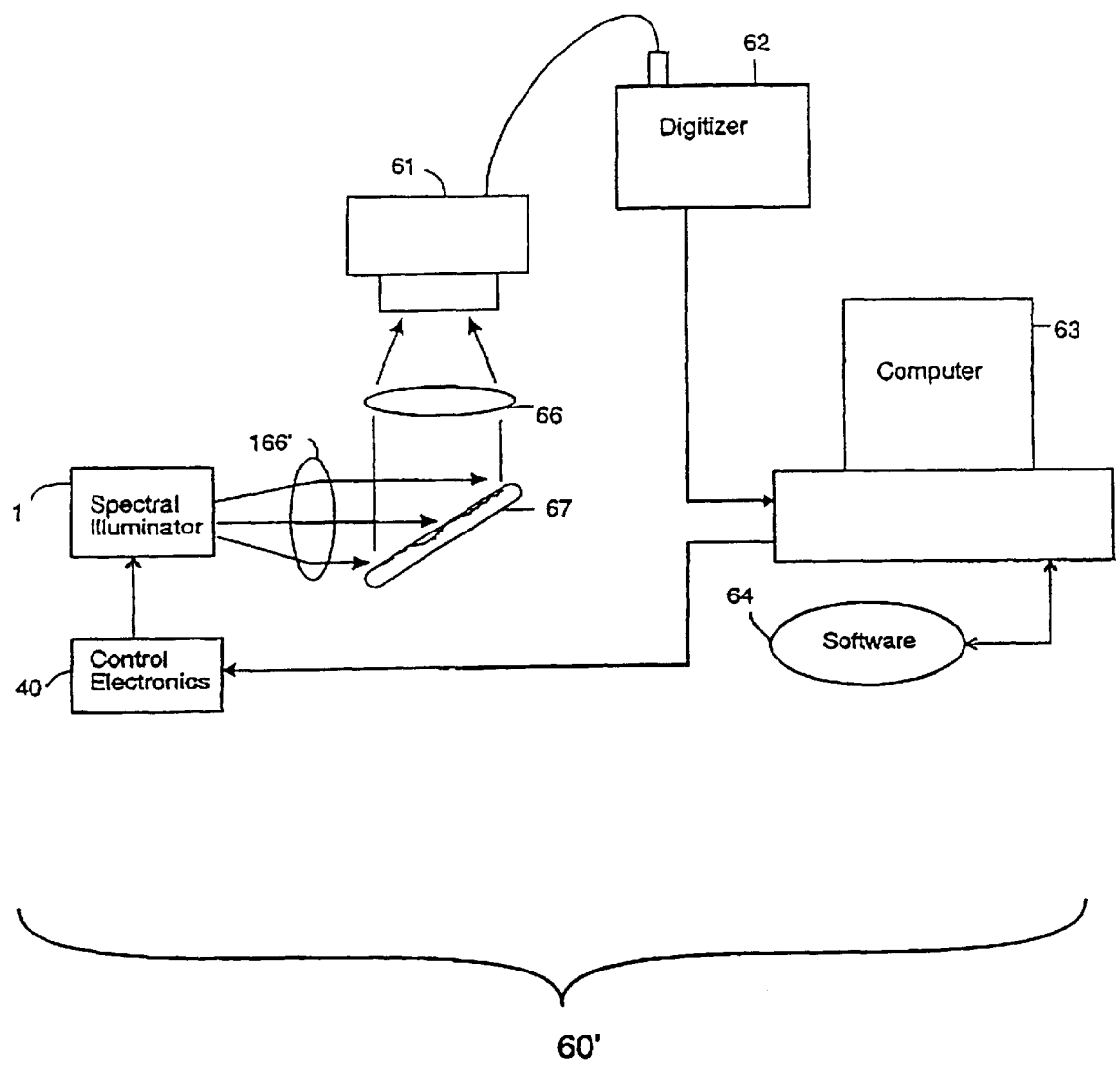

FIG. 1 is a diagrammatic representation of a first implementation of a spectral illuminator 1 suitable for use in the present invention. LED lamps 10$a$–$j$ produce light of various wavelengths that span the spectral range of interest (normally the photopic visible). Lenses 11$a$–$j$ collimate the light from each LED and bandpass filters 12$a$–$j$ provide spectral filtration of the various bands so that the light in each band has a very well-defined spectral range with much greater specificity than that defined by the LEDs themselves. Objective 13 re-images the collimated light from the various LED channels onto the tip of optical fiber 14. When light emerges from this fiber, it is imaged by lens system 15 and directed towards the sample without spectro-spatial artifacts;

FIG. 2 diagrammatically illustrates another implementation of a spectral illuminator 1 for use with the present invention, wherein LED lamps 10$a$–$j$ are placed at the focal plane of a spectrometer comprising reflective grating 31, lens system 32, and optional exit slit 33. Light emerging from the LEDs is spectrally selected by the grating according to the grating equation and the position of the LEDs, so that only a precisely regulated band enters multimode optical fiber 14 and passes to the sample through lens system 15;

FIG. 3 shows a block diagram of the electronics 40 used in a spectral illuminator in accordance with the invention, with control module 42, analog electronics 43$a$–$j$ producing signals 44a–j for driving the LEDs, an optional memory module 41 for storing information about several drive states, and digital interface 45;

FIG. 4a shows partly in block diagram form and partly diagrammatically a system 60 for obtaining spectral measurements of a sample 67 on a microscope 65 using the spectral illuminator 1 and associated control electronics 40, along with a video or digital camera 61, digitizer 62, computer 63 and software 64; and FIG. 4b shows partly in block diagram form and partly diagrammatically a system 60' for obtaining spectral measurements of non-microscopic sample 67 using the spectral illuminator 1 and its control electronics 40, along with a video or digital camera 61, lens 66, digitizer 62, computer 63 and software 64.

DETAILED DESCRIPTION OF THE PRESENTLY PREFERRED EMBODIMENTS

The preferred embodiment of the spectral illuminator uses LEDs with one LED per spectral channel. The light levels can be independently controlled by varying the drive currents, since the optical output of LEDs varies linearly with current, for low currents and low frequencies. It is vital to couple the light from all LEDs into a single beam, without spectral variation from point to point.

A first preferred embodiment of a spectral illuminator in accordance with the present invention is illustrated in FIG. 1. It depicts a system with ten spectral channels, but this is meant to be illustrative rather than restrictive, and systems may be built with any number of channels utilizing the same principles. The beam from each LED 10a–10j is collimated by lenses 11a–11j to produce a pupil plane at infinity, oriented parallel to a common optical axis. The light from the lenses then passes through bandpass filters 12a–12j to provide well-defined spectral outputs. The various LEDs, collimators and filters are tiled at the entrance aperture of a telescope 13, which images all rays of a shared propagation direction to a common point. An optical fiber 14 is placed at that point. The telescope causes the spatially distinct but parallel rays from the various LEDs to pass through a single point with various angles. The optical fiber randomizes the angular distribution, provided that the length of the fiber is long enough such that all rays undergo multiple reflections within it.

While a range of configurations are possible, most commonly the spectral channels will be in the range of 3 nm–20 nm per band, and there will be from 8 to 80 spectral bands overall. LEDs are not presently available with spectral widths narrower than about 35 nm, so it is normally necessary to use bandpass filters to further define the passband from each given LED. For example, in FIG. 1, there are 10 LEDs and bandpass filters with center wavelengths spanning the range 430 nm–655 nm at 25 nm intervals. Since the light is collimated at the point it passes through the bandpass filters, the spectral properties of those elements are not compromised.

The combination of each collimator 11a–11j and the telescope 13 comprises a magnifier with gain F2/F1, where F2 is the focal length of the telescope and F1 is the focal length of the collimator lens. The design of this assembly presents optical engineering problems as will be known to one skilled in the art of optical design. Primary goals are to produce a high efficiency in coupling light from the LED into the fiber, and to ensure the design is manufacturable without requiring unduly tight dimensional tolerances.

Use of a large diameter optical fiber is often favored since this enables capturing more light. Similarly, use of optical fiber with relatively high numerical aperture (NA) is favored in many designs, since the fiber NA limits the effective NA of the telescope. Higher NA means a shorter telescope may be employed, yielding a more compact assembly.

Choice of particular LEDs is dictated by the need for spectral coverage and high brightness. The latter is important since the overall brightness of the illuminator is proportional to the spectral radiance of the LED. It is possible to use bare LEDs of the type that emit vertically (normal to the chip surface), as well as to use packaged LEDs. Choice of one over the other will be dictated by the properties of available LED sources, as well as cost, ease of assembly, and other practical factors. Suitable LEDs include high-brightness LEDs from Stanley, Cree Research, Nichia, and KingBright. These are sometimes hyperbolically described as "ultrabright", "superbright", and the like. Cree provides LEDs at 430, 450, 470, 490, 505, and 525 nm, which between them cover the range 420–540 nm. Many manufacturers provide LEDs covering the range 525–680 nm and the near-IR range, as is well-known in the art, and one source of such LEDs is MarkTech Optoelectronics (Menands, N.Y.). When packaged LEDs can be used, the rays leaving the LED are refracted somewhat by the package, and it may be helpful in some cases to polish the LED front to be flat instead. The collimating lenses 11a–j are designed accordingly with the goal of maximizing the energy that is coupled into the fiber.

In one realization of the embodiment depicted in FIG. 1, the lenses 11 consist of 19 individual lenses, each with 25.4 mm focal length and diameter of 12.7 mm. They are tiled in a hexagonal close-packed arrangement within an overall diameter of 63.5 mm. Nineteen LEDs having wavelengths from 420–690 nm arranged at 15 nm intervals are situated behind the lenses, and nineteen interference filters having corresponding passbands are placed in front of the lenses. Mechanical mounting of the lenses and filters is accomplished using the space between them, so maximum packing density is achieved. The telescope consists of a lens with 65 mm diameter and 75 mm focal length, for a working NA of 0.397. The telescope couples the collimated light from these LEDs into a 3 M multimode fiber with a 1 mm core and an NA of 0.39 (ThorLabs, Newton N.J., part FT-1.0-UMT). The fiber length is 2 meters, and at the distal end an achromatic lens of 25.4 mm focal length and 22 mm diameter images the fiber tip to infinity. The output beam may be directly coupled into microscopes such as the Zeiss AxioPlan.

In many cases, it is preferable to use a lens array rather than individual lenses for each LED. The lenses can be plastic or glass, as long as the optical quality does not degrade the every instance, and the choice of one over the other will be dictated by cost, optical performance, and other engineering design factors known to those skilled in the art.

It is not essential in the design of FIG. 1 that all LEDs have the same size lens. Varying the numerical aperture (NA) of the LED collimation lens provides a means for adjusting the collection efficiency, and hence for tailoring the overall output of the system. Since different LEDs have different spectral radiance properties, this can be desirable. Adjustment of LED drive current is another means for balancing or tailoring the relative output powers of the various channels when each is set to its full-scale intensity setting, i.e., different LEDs can have different full scale intensity settings determined by their respective maximum LED drive currents.

The approach in U.S. Pat. No. 5,029,545 is another preferred embodiment of a spectral illuminator suitable for use in the present invention, and although it typically requires one to obtain the LEDs in chip form (which is inconvenient since they are normally supplied in packaged form), the arrangement is preferable because it has a higher theoretical optical efficiency and hence greater light output. Such a system is shown in FIG. 3.

It is possible to use other elements to realize the spectral illuminator, in concert with, or instead of, the optical components described above. Indeed, any spectral illuminator is suitable, so long as it provides a plurality of well-defined bands with minimal overlap, that span the spectral ranges of interest. The flux from each band must be adjustable and reasonably reproducible, and it must be possible to have multiple bands active at one time.

When any of the above arrangements are employed to realize the spectral illuminator, it is essential to scramble the resultant beam so that its output spatial pattern is free of spectral variations to the greatest extent possible. Otherwise, the illumination pattern will vary depending on the wavelengths used (i.e. on which LEDs are lit), and when images are taken, the overall signal at the detector will vary both due to the spatial patterns in the sample properties and due to spatial patterns in the illumination beam, and these patterns will be difficult or impossible to separate out later.

Suitable scrambling elements include without limitation multimode optical fibers, randomized optical fiber bundles, quartz-type or liquid-type light guides, or spatial scramblers comprising a tube-like enclosure whose internal surfaces are reflective. The latter can be constructed from a glass cylinder whose inner surface is silvered, or four strip-shaped first-surface mirrors arranged to form a rectangular cylinder, or a similar arrangement. Regardless of the cross-section shape, the tube length should be several times the tube width in order to adequately scramble the beam.

The launch optics must also be designed to provide an intensity distribution that does not vary from wavelength to wavelength. Among the acceptable approaches are to collimate or re-image the output of the scrambler using reflective optics; and to collimate or re-image the scrambler output using an achromatic or apochromatic lens system. When the scrambler output is re-imaged, one approach is to place the sample at the focus of the re-imaging optic, so all rays sharing a given propagation vector will image to the same point on the sample. Alternatively, the scrambler output can be re-imaged onto the sample using a relay lens system, although this typically produces a less uniform range of intensities across the sample. Other arrangements that are known in the optical design art are also acceptable for launch optics, so long as they produce an intensity distribution that does not vary significantly with wavelength band.

In any of the previous embodiments, it is possible to include plural light sources for a given spectral band if higher brightness is needed than is available from a single source. Two or more sources then contribute additively to the overall flux. For example, if two or more LED elements 10a–j and filter elements 12a–j in FIG. 1 address the same band, a greater flux is available. Note that in the grating-based system, the second LED must be displaced in the dimension transverse to the dispersion axis, so the flux it contributes is selected to have the proper wavelength.

It is possible to incorporate laser diode sources as well as LED sources in the spectral illuminator, using fiberized or nonfiberized laser sources. The illuminator can thereby include one or more spectral line laser sources as well as broad-band LED sources. Means for incorporating such sources include without limitation collimating the laser light and making it incident on the telescope along with the light from the LEDs; use of fiber couplers to join the laser with light from the LEDs; placing the laser amongst an array of LEDs at the appropriate location in the focal plane of a spectrometer; and use of dichroic elements to join the laser light with the collimated light from one or more LEDs coupled by any means whatsoever.

It is sometimes beneficial to incorporate a laser diode to provide illumination levels, or wavelengths, or modulation speeds that exceed the capability of available LEDs. At present, for example, Nichia sells a 400 nm laser diode which can be used to excite the Hoechst nuclear stain (of interest to microscopy users), but there is no source of 400 nm LEDs with comparable brightness. Of course, the pace of technical development is rapid in this area, with new LED and laser diode sources becoming available, each with power and wavelength capabilities that must be matched against the application at hand. The decision to incorporate laser diode elements along with the LEDs will be made according to the required flux levels, cost of the various components, and the needs of the intended application.

Similarly, it is possible to include non-diode laser sources, or even other lamp sources along with LED sources. Fibers can be used to bring the beam to a suitable place in the optics for combination with LED sources or with other laser sources. However, non-diode lasers do not normally have ready means for intensity control unless the source provides modulation means internal to itself. Incorporation of shutters, variable attenuators, and other beam control means is known in the art and will be appropriate when the application warrants their use.

As is well-known, the output flux from an LED varies with drive current, which provides a means for precisely selecting the output of each channel. Typically a DAC converter is used together with a current-output drive circuit, with one such circuit for each LED. Unused channels may be turned off entirely. The output of the array can be further time-modulated, to provide a blanking interval that may be useful in reading out digital cameras without need for a mechanical shutter, and for other purposes such as time-resolved fluorescence measurements. In the latter case, modulation circuitry may be used alone or combined with multiplying DACs to achieve higher modulation speeds. The circuitry used for this is well-known by those skilled in the art of electronic circuit design, and by those familiar with circuitry used for driving LEDs for communications and photonics applications.

The overall scheme of the electronics 40 is illustrated in FIG. 3, which shows a digital control module 42 that communicates with external control means via an interface 45 and generates signals 44a–44j by means of circuits 43a–43j. Optional digital storage element 45 contains drive information for one or more spectral weighting functions.

When the spectral illuminator is used in conjunction with a detector of some kind which has linear response, it is possible to use the detector to calibrate the illuminator. This makes use of the linear detector response to generate an in-situ calibration of the possibly nonlinear illuminator.

The detector is an imaging detector, meaning that the detector records the intensity at all locations across a two-dimensional grid of points. Such detectors include without limitation charge-coupled device (CCD) detectors, complementary metal-oxide semiconductor (CMOS) detectors, charge-injection device (CID) detectors, vidicon detectors, reticon detectors, image intensifier tube detectors, and pixelated photomultiplier tube (PMT) detectors. Some of these detectors have useful features, such as being able to read out only a portion of the image area when this is desired, or providing adjustable spatial resolution by means of binning several pixels together. These are consistent with the invention, and may be incorporated if this is deemed beneficial. Any detector which is an imaging type and has suitable properties such as spatial resolution, sensitivity, and signal-to-noise can be employed, and the choice of one detector over another will be made for the usual engineering reasons such as cost, size, quality, readout speed, and so on.

A system in accordance with the invention for making spectral image measurements with a microscope is illustrated in FIG. 4a. The spectral illuminator 1 is the embodiment of FIG. 2 and uses a grating to combine outputs from an array of LEDs. This light is spatially talc scrambled by a multimode optical fiber and the output from the fiber is then collimated by an achromatic lens, through which it passes to the transmitted light lamp port of a Zeiss AxioSkop (Thornwood, N.Y.). A Roper Scientific CoolSnap camera (Tucson, Ariz.) 61 is attached to the camera port, and is connected to a PC/pentium computer 63 that is also connected to the interface of the spectral illuminator. Software controls the illuminator and takes images from the camera.

In one preferred embodiment, the software first operates the illuminator to produce red, then green, then blue illumination, taking an image at each setting with the digital camera and merging them into a high resolution color image that is presented on the computer screen. This embodiment is a pathology workstation, and the images are of tissue samples. The RGB image is used in order to read the sample and identify features of interest. From the RGB image a pathologist selects certain cells which are believed to be cancerous or otherwise of interest, by selecting them or the region including them. The software then takes spectral cubes by programming the spectral illuminator to produce monochromatic light of a first wavelength, then a second, and so on, through the entire spectral range, while acquiring images at each spectral setting. The digital camera may be set to acquire only the region of interest (ROI) to the pathologist, so data acquisition is quite rapid. Typically, the ROI can be 1/10 of the image or less in either width or height, so only 1 percent or less of the image area. It is possible to acquire at nearly video rates, and the image cube of the ROI is often acquired in under two seconds.

From the spectral cube, a spectral weighting index is derived by projection pursuit, or by any other spectral algorithm of interest. These are described in the prior art such as "ISIS; An Information-Efficient Spectral Imaging System", by W. C. Sweatt, C. A. Boye, S. M. Gentry, M. R. Descour, B. R. Stallard, C. L. Grotbeck, *Imaging Spectrometry IV,* Proc. SPIE, Vol. 3438, pp. 98–106, San Diego, 1998; "Construction Of Filter Vectors For The Information-Efficient Spectral Imaging Sensor", by B. R. Stallard, S. M. Gentry, *Imaging Spectrometry IV,* Proc. SPIE, Vol. 3438, pp. 172–182, San Diego, 1998; "Spectrally Adaptive Light Filtering", by P. I. Shnitser, I. P. Agurok, Proc. SPIE, vol. 3140, p.117–27, 1997; "High Dimensional Feature Reduction via Projection Pursuit", by L. O. Jimenez, D. Landgrebe, TR-ECE 96-5, School of Electrical Engineering, Purdue University, West Lafayette, Ind. 47907-1285, 1995; all of whose contents are incorporated by reference in their entirety.

Principal component analysis is another way to generate spectral distributions that are of interest for a given type of scene. Convex-hull algorithms also generate spectral distributions of interest: this method seeks to identify what the spectra of various pure species would be, even if the species are always intermixed in the scene.

Once a spectral weighting index is derived, the spectral illuminator is then set to produce the spectral distribution specified by the spectral weighting index, and a two dimensional image of the sample is acquired. If several spectral measures are desired, then several exposures are taken. However, only one exposure is required for each spectral measure. These weighted images are analyzed for correlation with the spectral index, and cells throughout the image that are similar to the cells identified by the pathologist are identified. This identification can be performed by simply displaying the images obtained with the spectral weighting function (or by use of a false-color index for one image or by using a ratio or balance of several images taken with different weighted spectral indicia); or, it can be performed by highlighting the cells within an RGB display that have the trait of interest, so they appear as highlighted within an otherwise familiar lifelike image.

A similar workstation can be produced that is a general purpose bio-medical workstation capable of analyzing samples of blood and other vital fluids. In such a workstation, the invention is capable of providing RGB reference images; of taking full image cubes of the entire sample or of a representative portion; of developing spectral indices based on the data taken from the representative portion; then of rapidly acquiring images of the spectral indicia over a larger sample or over many samples. The ability to take and analyze spectral image cubes of representative samples enables one to overcome many of the problems that traditionally confound spectral imaging of complex biological samples, namely those problems related to the sample preparation, staining protocol, and subtle variations that arise due to uncontrolled factors such as pH and electrolyte levels. From the training set, the degree and nature of these variations is accomodated, and a more robust measurement or assay is obtained.

It is of great benefit that no additional apparatus is required to take the detailed spectral cube images, and that the subsequent data acquisition can proceed reliably and rapidly using the spectral measures abstracted from it, using only a very few exposures. This represents a substantial advantage over present alternatives for spectral imaging, in terms of speed, robustness, and cost.

One can show the equivalence of the image data obtained using the present invention to those obtained by prior art methods. In general, the signal induced at a detector by light in an infinitesimal spectral band centered at $\lambda$ and having width $d\lambda$ will be given by $$D(\lambda)=I(\lambda)\ S(\lambda)\ R(\lambda)\ d\lambda \qquad [1]$$

where $D(\lambda)$ is the signal produced at the detector, $I(\lambda)$ is the illumination flux, $S(\lambda)$ is the spectral response of the sample, and $R(\lambda)$ is the detector responsivity at wavelength $\lambda$.

$S(\lambda)$ may indicate reflection, transmission or scatter, depending on how the sample is being illuminated and viewed, (i.e. by a transmissive, reflective, or scattering arrangement). In the present context, these are equivalent so long as the wavelength of light is substantially unaltered by its interaction with the sample.

It is possible to rewrite the above equation in terms of discrete bands, provided that the bands are chosen to be sufficiently narrow that neither the illumination, sample response, or detector responsivity varies greatly within a given band. Then one may write the expression for the contribution from light in the j-the band as $$D(j)=I(j)\ S(j)\ R(j)\ d\lambda \qquad [2]$$

One normalizes spectral readings against a standard such as a white card (for reflection measurements) or a transparent reference (for transmission measurements). This normalization is performed on a band-by-band basis, and typically for the standard $S(\lambda)=1$, leading to a signal of $$D(j)=I(j) R(j) d\lambda \qquad [3]$$

when the standard is read. This allows one to measure the normalized sample property $S(j)$ by taking the ratio of the detector readings when the sample is present, relative to when the standard is present, as:

$$S(j)_{measured}=D(j)_{sample}/D(j)_{standard}=I(j) S(j) R(j) d\lambda_j/I(j) R(j) d\lambda_j=S(j) \qquad [4]$$

The present invention uses this same method to determine the image cube for a sample. One illuminates with each wavelength band in turn and observes the detector reading $D(j)$, under both sample and standard conditions; the ratio yields the sample response $S(j)$.

But the readings $D(j)_{standard}$ are especially significant for the present system. They indicate the reading for a given spectral band at the LED current setting used for that exposure. Since the LED output is variable, it is possible to adjust the LED current setting so as to attain a sought-for reading at the detector, which we denote as K. By doing so in all bands, and recording the drive current settings $C(j)$ required to meet this condition, one can calculate a calibration table of scale factors $\alpha(j)$:

$$\alpha(j)=K/C(j) \qquad [5]$$

The scale factor $\alpha(j)$ is the detector response per unit of LED drive current in band j, and it will be used in realizing the spectral weighting functions, as described below.

The spectral weighting function WF and its distribution $F(j)$ are derived from the image cube in an entirely conventional manner, using all the methods that are familiar to one skilled in the art of spectroscopy and multispectral image analysis. Given a spectral weighting function with a spectral distribution $F(j)$ for a specified set of bands $\lambda_j$, the spectral index for a sample with response $S(j)$ is given by:

$$WF=\Sigma_{all\ j} [S(j) F(j) d\lambda_j] \qquad [6]$$

where $\Sigma_{all\ j}$ denotes the summation over all bands j.

Prior-art methods obtain this by first measuring the detector response $D(j)$ under standard conditions, then, when the sample is present, dividing to obtain the sample spectrum $S(j)$, and finally weighting the readings $S(j)$ by the various factors $F(j)$ and numerically integrating in accordance with Equation 5.

In contrast, the present invention adjusts the settings of the spectral illuminator to produce an illumination spectrum with the property that $$I(j)=F(j)/D(j) \qquad [7]$$

That is, the illumination distribution has the shape of the spectral weighting distribution $F(j)$, divided by the detector responsivity $D(j)$.

When the sample is imaged under this controlled illumination, the total signal at the detector D is given by $$D=\Sigma_{all\ j} [I(j) S(j) D(j) d\lambda_j]$$
$$=\Sigma_{all\ j} [F(j)/D(j)*S(j)*D(j) d\lambda_j]$$
$$=\Sigma_{all\ j} [S(j) F(j) d\lambda_j]=WF \qquad [8]$$

The detector directly measures the weighting function, without need for breaking the light up into its constituent spectrum and numerically analyzing it. The result is an optical, rather than numerical, evaluation of the spectral weighting function, with enormous increase in speed and efficiency.

The LED current settings which realize the required illumination spectral distribution can be calculated directly from the tabulated $\alpha(j)$ values; the proper LED current setting for band j is simply $F(j)/\alpha(j)$.

The importance of this result cannot be overstated. It renders spectral imaging practical for a wide range of uses where the presently-available alternatives are rejected by all but the research community as far too cumbersome. By substituting a direct optical measurement for an extensive numerical computation, i.e. by replacing the acquisition and processing of an entire image cube (which may require extensive calculations on 128 megabytes of data or more) with the acquisition of a very few precisely weighted spectral images that directly capture the information of interest, the traditional barriers to multispectral imaging are completely removed.

For the first time, the process of multispectral imaging can proceed in real-time, eliminating the normal delay of several seconds per image (or the alternative need for specialized, expensive image processing hardware). The need for vast amounts of computer memory are eliminated, since typically only 2–5 bands are required—scarcely more than is used in a normal display. A high degree of flexibility is gained, since the same apparatus can be used to perform the spectral calibration, obtain the informational RGB images, determine the spectral index of interest, and acquire the weighted images at high speed using the index and calibration performed earlier.

Another embodiment is shown in FIG. 4b. Here light from a spectral illuminator is fed through illumination optics to produce a spectrally uniform illumination pattern at a macroscopic sample which is then imaged with a lens by a camera. The camera's digitized output is fed to a computer which produces images and digitized data of the sample.

The system can be used for hyperspectral imaging, or for producing an RGB image of the sample, or for imaging the sample in XYZ colorimetric space, from which representations such as L*a*b and Luv may be derived without loss or approximation.

In these cases, it is important to understand that the tristimulus curves are not themselves the weighting function of interest. Recall that the goal is to measure the amount of energy that a detector (like the eye) having tristimulus response would see when the sample is illuminated with a standard illuminant such as CIE A, or daylight, or some other reference illuminant of interest. The spectral weighing function is thus the band-by-band product of a reference illumination spectrum, times one of the tristimulus functions. The result is that one obtains images of a scene as it would appear under various controlled illuminants, in accurate calorimetric coordinates.

In detail, the desired weighting function $F(j)$ is the product of the $$F(j)=L(j)*X(j) \ \{X \text{ tristimulus reading}\} \qquad [9a]$$

$$F(j)=L(j)*Y(j) \ \{Y \text{ tristimulus reading}\} \qquad [9b]$$

$$F(j)=L(j)*Z(j) \ \{Z \text{ tristimulus reading}\} \qquad [9c]$$

where $L(j)$ is the spectrum of the desired illuminant in band (j), and $X(j)$, $Y(j)$, and $Z(j)$ are the usual tristimulus functions, evaluated in band (j). And to realize this measurement, one sets the spectral illuminator so that the bands are further corrected for the detector's spectral response D(j), as discussed above:

$$I(j)=L(j)*X(j)/\alpha(j) \quad \{X \text{ tristimulus reading}\} \quad [10a]$$

$$I(j)=L(j)*Y(j)/\alpha(j) \quad \{Y \text{ tristimulus reading}\} \quad [10b]$$

$$I(j)=L(j)*Z(j)/\alpha(j) \quad \{Z \text{ tristimulus reading}\} \quad [10c]$$

The image thus obtained will then be the desired X, Y or Z value as would be expressed under the specified standard illumination such as CIE A, daylight, and so on.

Prior-art systems having only a few LEDs with broad spectral response have been designed to match the X, Y or Z functions without regard for the illumination conditions under which they are evaluated. Effectively, this means the calorimetric values were obtained under a "greybody" illuminant, which is not physically appropriate for most cases, and is not normally desired.

The present system, with precise and independent spectral control over each band, can incorporate much more subtle effects in its action. It can readily incorporate the effect of a suitable illumination function, or of various illuminants as desired, to assess-the calorimetric values under a chosen illumination.

The same system can be used to image the sample in terms of spectral weighting functions that are indicia of a state or condition that is peculiar to the type of sample being imaged, and are determined by a representative measurement of the sample. As discussed in the previous embodiment, the process for doing so involves the generation of an image cube, development of a weighting function F( ), calculation of the LED current settings that realize the desired controlled illumination state I(j), followed by direct imaging of the weighted spectral index using that controlled illumination. The different modes are produced by software selection of the spectral illumination function I(j) produced by the spectral illuminator.

A macro imaging system has utility in endoscopic applications such as surgery, for several reasons. First, the use of a sequential illumination system with a monochrome camera produces sharper images than conventional RGB cameras, since the latter use a mosaic of color spots on the detector that degrade its spatial resolution by a factor of 4 compared to a monochrome detector of the same size. So, sharper pictures are obtained for a given endoscope detector size, or alternatively a smaller detector can be used. Then, the surgeon may use the spectral weighting functions to identify the spectrum of a feature of interest (such as a lesion or a cancerous piece of tissue), by taking an image cube of the region of interest. This is considerably faster than for competitive techniques, since the region is normally only a small portion of the image, and the spectral illuminator can change its output in microseconds. When the spectral signature of the feature is identified (by principal component analysis, projection pursuit, or other algorithms that are known in the art), the spectral illuminator can rapidly and efficiently visualize the scene and continue hunting for other areas that have the desired spectral properties. The task of searching for low-probability events is practical since each image requires only a few exposures, one with the illuminator set to each of the spectral weighting functions of interest.

Another application of this invention is in a retinal imaging station. The spectral illuminator and associated launch optics are used to generate illumination that is spectrally agile and essentially free from variations in spatial pattern between spectral bands. A camera such as a fundus camera is used to image the retina. RGB images can be obtained by sequentially illuminating with the three color primaries while taking images with a monochrome detector. Spectral image cubes may be obtained, and the system calibrated, by sequential illumination of the various spectral bands while imaging with the monochrome imaging detector. It is also possible to capture images of weighted spectral indicia in rapid time sequence, while imaging with the monochrome detector.

In this example, the multiple operating modes provide powerful versatility. The invention enables one to obtain reference images, images of indicia of interest which can be overlayed in false color on top of the reference RGB images for display purposes, and full image cubes for the most detailed analysis. There is no need for additional equipment, which eliminates bulk, expense, and complexity. The ability to take all these images at video frame rates, and in the case of the weighted indicia, to obtain vast information in only a few frames, minimizes the problem of eye movement and/or the need to register various image bands later in software. From the perspective of the clinician and patient alike, the simplicity and speed that accrue from this invention are a significant benefit over present alternatives such as interferometric or laser-based opthalmic imaging systems.

It can often be useful to incorporate bands which are spectrally distinct from the visible range to improve the specificity of the spectral index. That is, adding other spectral bands to the visible bands may enhance the ability to discriminate between different types of samples, or to quantify the properties of a sample. These bands are included in the image cube, and analyzed when determining the spectral index. Although they are spectrally distinct, there is no modification to the method or mathematics that is employed. If the band is useful in classifying the sample regions, it is included in the spectral weighting function and that element is turned on proportionally to its presence in that function for each exposure.

This is readily achieved in the near-infrared range, where LEDs and laser diodes are available in bands near 730 nm, 780 nm, 830 nm, 940 nm, and others. The choice to include one or more such bands is application-specific. For example, in the endoscopy embodiment, it may be beneficial to include wavelength bands at which tissue reflectivity tends to vary strongly according to the amount and oxygenation of hemoglobin, as well as adjacent bands. There is a great deal of prior art on the use of near-infrared spectroscopy to quantify total hemoglobin, blood oxygenation, blood sugar levels, and the like. This art teaches specific spectral bands in the near-infrared for this purpose. These bands may be included with visible illuminants, to enhance the selectivity of the spectral weighting functions that discriminate between different sample states or properties. The spectral illuminator is then used to realize such weighting functions and directly image the sample properties in these terms.

The use of medical examples is not meant to suggest that this is the sole or predominant use of the present invention. Similar benefits accrue in the use of borescopes for industrial inspection, in reflected-light microscopy for semiconductor and materials measurements, and in any endeavor where spectral signatures enable discrimination between sample regions or quantify sample properties. One such application is in the field of counterfeit detection, since in general the dyes, paints, and materials used in a counterfeit will not match the genuine article at all wavelengths even if the overall visual appearance is quite similar. The phenomenon whereby objects appear similar to the eye under one set of lighting, but appear quite different under another set of lighting, is termed metamerism and can be used to great advantage in this context. A spectral weighting function that maximally illuminates in the spectral regions where the genuine article and the fake are different, will highlight these distinctions and make them readily apparent. The present invention provides a means for at once identifying the weighting function (through taking of a spectral image cube and its subsequent analysis on a computer), and then providing essentially real-time imaging of the possible counterfeit objects using that derived spectral weighting function (by having the spectral illuminator provide the weighted illuminants while imaging the sample).

It is also possible to alternate the spectral illuminator between one spectral weighting function and another, at a rate of a few cycles per second, so that one can view the object directly (or in the eyepieces of the microscope) in a way that will highlight the objects of interest by maximizing the visual contrast between settings for objects with the desired spectral distribution. Ideally, the spectral weighting function should take account of the disparity between the detector that was used to determine the optimal spectral weighting function, and the spectral sensitivity of the human eye, and adjust the settings of each spectral band in the spectral illuminator accordingly.

Except as specifically noted, a range of specific designs, components and optical elements may be used to realize the invention, and such alternatives and equivalents may be employed without deviating from the spirit of the invention, as will be apparent to one skilled in the field of optical design and instrument design.

It should also be understood that any reference in the claims or the specification to a "means for" accomplishing a function of an apparatus or a step in a process is intended to encompass any implementation thereof known to those of skill in the art and that no limitation whatsoever on the manner of said implementation is intended, except insofar as necessary to achieve the intended results of the invention. For example, any reference in the claims to a computer having "means for" accomplishing a function is intended to encompass any software or hardware implementation capable of accomplishing that function.

Thus various embodiments and components have been shown for constructing this invention, and these may be used singly or in combination, or with other elements known in the arts of optical design, color science, and instrument design. It is understood that these and other such combinations, substitutions, and alternative embodiments may be undertaken according to the requirements and materials at hand without deviating from the spirit of the invention, the scope of which is to be limited only by the claims appended hereto.

We claim:

1. An imaging spectroscopy system, comprising:
   a spectral illuminator that emits light in a plurality of spectral bands within a predefined spectral range, with the intensity of light in each spectral band being independently adjustable;
   drive circuitry that controls the flux in each spectral band of the spectral illuminator;
   scrambling optics having a length sufficient to spatially homogenize the distribution of light emitted by the spectral illuminator;
   beam delivery optics that direct the spatially homogenized light from the scrambling optics to form an illumination pattern at a sample, wherein the length of the scrambling optics cause the illumination pattern to be substantially free of variation as a function of wavelength within the predefined spectral range;
   receiver optics that receive light which has interacted with the sample and form an image of the sample at a focal plane;
   an imaging detector located at the focal plane for detecting and spatially resolving the image of the sample; and
   a computer in communication with the drive circuitry and the imaging detector for controlling the drive circuitry and receiving data from the imaging detector.

2. The system of claim 1 wherein the spectral illuminator emits light in the plurality of bands simultaneously, with different intensity levels in each active band.

3. The system of claim 1 wherein the spectral illuminator comprises an array of light sources coupled to an output slit by means of a dispersive element, wherein each light source corresponds to one of the spectral bands.

4. The system of claim 3, wherein the array of light sources is an array of LEDs and the dispersive element is a grating.

5. The system of claim 1, wherein the scrambling optics comprise a multimode optical fiber.

6. The system of claim 5, wherein the multimode optical fiber has a length of at least about 2 m.

7. The system of claim 5, wherein the multimode optical fiber has a core diameter of at least about 1 mm.

8. The system of claim 1, wherein the scrambling optics comprise a randomized fiber optic bundle.

9. The system of claim 1, wherein during operation the computer generates from the detector data a color image of the sample and an image of the sample for a selected spectral weighting function.

10. The system of claim 1, further comprising a display coupled to the computer for displaying a full image cube and a color image derived from the detector data.

11. The system of claim 1, wherein during operation the computer determines at least one spectral weighting function based on the detector data.

12. The system of claim 1, wherein during operation and in response to a user-selected spectral weighting function, the computer causes the spectral illuminator to emit light corresponding to a calibrated spectral weighting function that compensates the selected spectral weighting function for the spectral response of the imaging spectroscopy system.

13. The system of claim 1, wherein the imaging spectroscopy system is part of a pathology work station.

14. The system of claim 1, wherein the imaging spectroscopy system is part of a blood analysis work station.

15. The system of claim 1, wherein the imaging spectroscopy system is part of an endoscopy imaging station.

16. The system of claim 1, wherein the imaging spectroscopy system is part of a retinal imaging station.

17. An imaging spectroscopy system comprising:
   a spectral illuminator which during operation emits light in a plurality of spectral bands within a predefined spectral range, with the intensity of light in each spectral band being independently adjustable;
   optics for directing the light emitted by the spectral illuminator to form an illumination pattern on a sample, wherein during operation the sample interacts with the illumination pattern to produce signal light;
   an imaging detector positioned to detect and spatially resolve the signal light from the sample; and
   a computer coupled to the spectral illuminator and the imaging detector, wherein during operation the computer generates a color image of the sample and an image of the sample for a selected spectral weighting function based on data produced by the detector.

18. The system of claim 17, wherein the color image is an RGB image.

19. The system of claim 17, wherein the selected spectral weighting function includes intensity at multiple spectral bands.

20. The system of claim 17, wherein the selected spectral weighting function is a spectral index indicating the presence of a certain trait in the sample.

21. The system of claim 17, further comprising a display coupled to the computer for displaying the color image and the image of the sample for the selected spectral weighting function, wherein during operation the display overlays the images in response to a request from the computer.

22. An imaging spectroscopy system comprising:
a spectral illuminator which during operation emits light in a plurality of spectral bands within a predefined spectral range, with the intensity of light in each spectral band being independently adjustable;
optics for directing the light emitted by the spectral illuminator to form an illumination pattern on a sample, wherein during operation the sample interacts with the illumination pattern to produce signal light;
an imaging detector positioned to detect and spatially resolve the signal light from the sample; and
a computer coupled to the spectral illuminator and the imaging detector, wherein during operation the computer generates a color image of the sample and a full image cube of the sample.

23. The system of claim 22, further comprising a display coupled to the computer for displaying the color image and the full image cube.

24. An imaging spectroscopy system comprising:
a spectral illuminator which during operation emits light in a plurality of spectral bands within a predefined spectral range, with the intensity of light in each spectral band being independently adjustable;
optics for directing the light emitted by the spectral illuminator to form an illumination pattern on a sample, wherein during operation the sample interacts with the illumination pattern to produce signal light;
an imaging detector positioned to detect and spatially resolve the signal light from the sample; and
a computer coupled to the spectral illuminator and the imaging detector, wherein during operation the computer determines at least one spectral weighting function based on data produced by the detector.

25. The system of claim 24, wherein the determined spectral weighting function includes intensity at multiple spectral bands.

26. The system of claim 24, wherein the detector data comprises data for the sample at each of a plurality of pure spectral bands.

27. The system of claim 26, wherein the determined spectral weighting function is a spectral index indicating the presence of a certain trait in the sample.

28. The system of 26 wherein the computer determines the spectral index using at least one of principal component analysis, projection pursuit, independent component analysis, and convex-hull analysis.

29. The system of claim 24, wherein the signal light produced by the interaction between the illumination pattern and the sample comprises light transmitted through the sample, and wherein the imaging detector is positioned to detect and spatially resolve the light transmitted through the sample.

30. The system of claim 24, wherein the signal light produced by the interaction between the illumination pattern and the sample comprises light reflected by the sample, and wherein the imaging detector is positioned to detect and spatially resolve the light reflected by the sample.

31. An imaging spectroscopy system comprising:
a spectral illuminator which during operation emits light in a plurality of spectral bands within a predefined spectral range, with the intensity of light in each spectral band being independently adjustable;
optics for directing the light emitted by the spectral illuminator to form an illumination pattern on a sample, wherein during operation the sample interacts with the illumination pattern to produce signal light;
an imaging detector positioned to detect and spatially resolve the signal light from the sample; and
a computer coupled to the spectral illuminator and the imaging detector, wherein during operation and in response to a user-selected spectral weighting function, the computer causes the spectral illuminator to emit light corresponding to a calibrated spectral weighting function that compensates the selected spectral weighting function for the spectral response of the imaging spectroscopy system.

32. An imaging spectroscopy method comprising:
providing light in a plurality of spectral bands within a predefined spectral range, with the intensity of light in each spectral band being independently adjustable;
scrambling the light to spatially homogenize the light from the different spectral bands;
forming an illumination pattern derived from the spatially homogenized light on a sample, wherein the illumination pattern is substantially free of variations as a function of wavelength within the predefined spectral range; and
spatially resolving an image of the sample produced by its interaction with the illumination pattern.

33. An imaging spectroscopy method comprising:
providing light in a plurality of spectral bands within a predefined spectral range, with the intensity of light in each spectral band being independently adjustable;
forming an illumination pattern derived from the light on a sample;
spatially resolving an image of the sample produced by its interaction with the illumination pattern for each of multiple intensity distributions of the spectral bands; and
generating a color image of the sample and an image of the sample for a selected spectral weighting function based on the spatially-resolved images.

34. The method of claim 33, further comprising overlying the color image and the image of the sample for the spectral weighting function in a display.

35. An imaging spectroscopy method comprising:
providing light in a plurality of spectral bands within a predefined spectral range, with the intensity of light in each spectral band being independently adjustable;
forming an illumination pattern derived from the light on a sample;
spatially resolving an image of the sample produced by its interaction with the illumination pattern for each of multiple intensity distributions of the spectral bands; and
determining a spectral index indicating the presence of a certain trait in the sample based on the spatially resolved images.

36. A method of imaging comprising:

obtaining images of a first sample at a plurality of pure spectral bands by controlling a spectral illuminator to sequentially produce light in each of said plurality of pure spectral bands and recording images of the first sample under these conditions using an imaging detector;

determining one or more spectral weighting functions that indicate a property or attribute of a sample, using the images of the first sample; and measuring the value of one or more of said spectral weighting functions in a subsequent sample by repeating the following steps for each of said one or more spectral weighting functions:
  i) adjusting the spectral illuminator to produce light whose spectral flux distribution is based upon the spectral weighting function;
  ii) illuminating the sample with light from the spectral illuminator as adjusted in step (i); and
  (iii) recording an image of the second sample under these illumination conditions using the imaging detector.

37. The method of claim 36, wherein each spectral weighting function comprises a plurality of components in different spectral bands.

38. The method of claim 36, wherein plural spectral weighting functions are determined.

39. The method of claim 36 wherein the spectral weighting function is determined based on at least one of principal component analysis, projection pursuit, independent component analysis, and convex-hull analysis.

40. A method of spectral imaging comprising:

obtaining reference images at a plurality of pure spectral bands by controlling a spectral illuminator to sequentially produce light in each of said plurality of pure spectral bands and recording an image under these conditions using an imaging detector;

calibrating the system spectral response using the reference images; and measuring the value of one or more spectral weighting functions in the sample by repeating the following steps for each spectral weighting function:
  i) adjusting the spectral illuminator to produce light whose spectral flux distribution is based upon the calibration data and the spectral weighting function;
  ii) illuminating the sample with light from the spectral illuminator as adjusted in step (i); and
  (iii) recording an image of the sample under these illumination conditions using the imaging detector,
  wherein each of said one or more spectral weighting functions indicates a property or attribute of the sample.

41. The method of claim 40, wherein each spectral weighting function comprises a plurality of components in different spectral bands.

* * * * *

UNITED STATES PATENT AND TRADEMARK OFFICE
CERTIFICATE OF CORRECTION

PATENT NO. : 6,690,466 B2
DATED : February 10, 2004
INVENTOR(S) : Peter J. Miller and Clifford C. Hoyt It is certified that error appears in the above-identified patent and that said Letters Patent is hereby corrected as shown below:

Column 10,
Line 45, replace "$\lambda$and" with -- $\lambda_o$and --
Line 46, insert a space between "d$\lambda$" and "will"
Line 47, replace "$D(\lambda)=I(\lambda) \, S(\lambda) \, R(\lambda) \, d(\lambda)$" with -- $D(\lambda_o)=I(\lambda_o) \, S(\lambda_o) \, R(\lambda_o) \, d\lambda$ --
Line 64, replace "j-the" with -- j-th --.
Line 65, replace "d$\lambda$" with -- d$\lambda_j$ --

Column 11,
Line 5, replace "d$\lambda$" with -- d$\lambda_j$ --

Column 17,
Line 56, insert -- claim -- after "of" and replace "26" with -- 27 --

Signed and Sealed this

Fifteenth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,690,466 B2
DATED : February 10, 2004
INVENTOR(S) : Peter J. Miller and Clifford C. Hoyt It is certified that error appears in the above-identified patent and that said Letters Patent is hereby corrected as shown below:

Title page,
Item [56], References Cited, U.S. PATENT DOCUMENTS,
"5,424,545" reference, replace "6/1995" with -- 1/1995 --.
OTHER PUBLICATIONS,
"Sweatt et al." reference, replace "Vo." with -- Vol. --.
Item [57], ABSTRACT,
Line 16, delete """ after "sample" and replace "measure" with -- measures --.

Column 1,
Line 29, replace "interferomieters" with -- interferometers --.

Column 2,
Line 7, replace "illdefined" with -- ill-defined --.

Column 3,
Line 46, insert -- be -- between "may" and "on".
Line 53, delete """ before "each".

Column 6,
Line 51, between "the" and "every" insert -- efficiency of optical coupling into the fibers. Mirrors may be used instead of lenses at each and --.

Column 9,
Line 14, delete "talc" after "spatially".

Signed and Sealed this

Twenty-ninth Day of November, 2005

JON W. DUDAS
*Director of the United States Patent and Trademark Office*